(12) United States Patent
Xiang

(10) Patent No.: US 11,911,169 B2
(45) Date of Patent: Feb. 27, 2024

(54) SYSTEMS AND METHODS FOR ENHANCED ENCODED SOURCE IMAGING

(71) Applicant: Children's Hospital Medical Center, Cincinnati, OH (US)

(72) Inventor: Jing Xiang, Mason, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 204 days.

(21) Appl. No.: 17/476,518

(22) Filed: Sep. 16, 2021

(65) Prior Publication Data
US 2022/0000412 A1  Jan. 6, 2022

Related U.S. Application Data

(63) Continuation of application No. 16/157,780, filed on Oct. 11, 2018, now Pat. No. 11,147,501.

(60) Provisional application No. 62/571,322, filed on Oct. 12, 2017.

(51) Int. Cl.
| A61B 5/05 | (2021.01) |
| A61B 5/00 | (2006.01) |
| A61B 5/245 | (2021.01) |
| A61B 5/374 | (2021.01) |
| A61B 5/055 | (2006.01) |

(52) U.S. Cl.
CPC ............. *A61B 5/374* (2021.01); *A61B 5/245* (2021.01); *A61B 5/4094* (2013.01); *A61B 5/7225* (2013.01); *A61B 6/466* (2013.01); *A61B 5/055* (2013.01); *A61B 5/7253* (2013.01); *A61B 5/726* (2013.01); *A61B 5/743* (2013.01)

(58) Field of Classification Search
CPC ......... A61B 5/055; A61B 5/245; A61B 5/374; A61B 5/4094; A61B 5/7225; A61B 5/7253; A61B 5/726; A61B 5/743; A61B 6/466
See application file for complete search history.

(56) References Cited

U.S. PATENT DOCUMENTS

| 2006/0227020 A1 | 10/2006 | Adachi |
| 2014/0343397 A1* | 11/2014 | Kim .................... G01R 33/445 600/409 |
| 2016/0213258 A1 | 7/2016 | Lashkari et al. |

* cited by examiner

*Primary Examiner* — Mark D Remaly
(74) *Attorney, Agent, or Firm* — BakerHostetler

(57) ABSTRACT

A frequency encoded source imaging system includes an EEG or MEG sensor array and a processing system for analyzing the signals from the sensor array in at least two different frequency bands, where the analysis is localized with respect to a three-dimensional grid corresponding to the portion of the human body. Alternately, a frequency encoded source imaging system includes an EEG or MEG sensor array and a processing system for analyzing the signals from the sensor array in a high-definition frequency band comprising frequencies greater than 70 Hz, where the analysis is localized with respect to a three-dimensional grid corresponding to the portion of the human body.

18 Claims, 8 Drawing Sheets

SYSTEMS AND METHODS FOR ENHANCED ENCODED SOURCE IMAGING

CROSS REFERENCE TO RELATED APPLICATIONS

This application is a continuation of U.S. patent application Ser. No. 16/157,780 filed Oct. 11, 2018, which claims the benefit of U.S. provisional application Ser. No. 62/571,322 filed Oct. 12, 2017, the entire contents of each of which being incorporated herein by reference.

BACKGROUND

The current disclosure relates to electric/magnetic source imaging.

Electroencephalography (EEG) is an electrophysical monitoring method to record electrical activity of the brain (or other body parts). Electrodes are paces along the body part and EEG measures voltage fluctuations. In the brain the voltage fluctuations are the result of ionic currents within the brain. EEG may be used to diagnose epilepsy, which causes abnormalities in EEG readings. EEG may also be used to diagnose or monitor sleep disorders, depth of anesthesia and other brain activities or effects on the brain.

Magnetoencephalography (MEG) is an imaging technique for mapping brain (or other body parts) activity by recording magnetic fields produced by electrical currents occurring in the brain. MEG uses very sensitive magnetometers such as arrays of SQUIDs (superconducting quantum interference devices) or arrays of SERF (spin exchange relaxation-free) magnetometers.

With a conventional single frequency source scanning, the signals recorded from an EEG or MEG sensor array are limited to one frequency range or band. In particular, the signals from the brain or heart are conventionally digitalized in a narrow frequency range and are then analyzed in one frequency range, which is commonly in 1-70 Hz.

SUMMARY

Embodiments of the current disclosure localizes the source of electric/magnetic signals detected by an electric/magnetic source imaging sensor array. The conventional method for diagnosis and treatment of epilepsy using electric/magnetic source imaging is visual identification of epileptic spikes in 14 to 70 Hz. Embodiments of the current disclosure, on the other hand, can detect epileptic activities in 0.0000001 Hz-20,000 Hz, which can significantly change the clinical outcomes (e.g., increasing post-operative seizure freedom by using high frequency EEG/MEG signals for pre-operative workup for epilepsy surgery). Embodiments of the current disclosure may also combine such high-resolution EEG/MEG (e.g., greater than 70 Hz resolution and upwards of 20,000 Hz resolution) with 3D localization.

Embodiments of the current Disclosure localize and visualize electrical and/or magnetic signals in at least two frequency ranges or bands. The signals are typically detected by a sensor array, which include at least two electrodes and/or magnetic sensors. Embodiments of the current disclosure will analyze signals in multiple (>2) frequency bands from very low to very high, and perform volumetric scanning of the sources of the signals in each frequency band. To scan sources for signals in multiple frequency bands, a three-dimensional (3D) grid is created for a source image. Sources at each position of the 3D grid will be analyzed. The frequency signature and source strength will be analyzed, quantified and stored for each position. Embodiments of the current disclosure further include the function to have multiple-parameters per position within the 3D grid (e.g., source strength, probability, and signal frequency bands are included as parameters for each position). Each position within the 3D grid will become as a voxel in the resulted source image. If signals from more than one frequency band are detected from the same grid position, signals with higher frequency will take the priority by default although the user of this method can change this behavior. To distinguish sources in different frequency bands, each frequency of the sources may be encoded with a unique characteristic (e.g., color, texture, or pattern). Embodiments of the current disclosure further include at least two sets of color (or other characteristic) tables for encoding frequency and other parameters for visualization of source signals in multiple frequency bands. Multiple color-coding may provide the capability to visualize the strength and frequency signatures of the source signals at each position of the 3D grid. Embodiments of the current disclosure may provide 3D patterns for clinicians to identify lesions or dysfunctions in the human body including in brain, heart and other organs. Since signals in medical fields are typically in a narrow and median (e.g. brain signals in 3-70 Hz) frequency range, signals in the low and high frequency ranges may be new biomarkers for clinical diagnosis and treatment.

In an aspect of the current disclosure, a frequency encoded source imaging system includes: a sensor array comprising a plurality of electrode and/or magnetic sensors where the sensor array is capable of being placed about a portion of a human body, and where the sensors are adapted to detect signals indicative of electrical and/or magnetic fluctuations present in a portion of the human body; and includes a processing system for analyzing the signals from the sensor array in at least two different frequency bands, where the analysis is localized with respect to a three-dimensional grid and/or multi sources corresponding to the portion of the human body. Likewise it is an aspect of the current disclosure to provide a method for frequency encoded source imaging that includes the steps of (a) providing a sensor array that includes a plurality of electrodes and/or magnetic sensors; (b) detecting by the sensors signals indicative of electrical/magnetic fluctuations present in a portion of a human body about which the sensor array is arranged; (c) analyzing the signals from the sensor array in at least two different frequency bands; and (d) localizing the analysis with respect to a three-dimensional grid corresponding to the portion of the human body.

In a more detailed embodiment the processing system and a display device are configured to display a color-coded three-dimensional image corresponding to the localized analysis of the signals in the at least two different frequency bands. In yet a further detailed embodiment, the three-dimensional grid includes a plurality of grid positions, and the processor is configured, for each grid position, to analyze and quantify the frequency signature and source strength for each of the at least two different frequency bands. And in yet a further detailed embodiment, the display device displays colors or characteristics corresponding to which of the at least two different frequency band have the highest source strength for each grid position.

Alternatively or in addition, the processing system includes at least two parallel processing pipelines, a first pipeline dedicated at least in part to the analyzing the signals from the sensor array in at least two different frequency bands, and a second pipeline dedicated at least in part to localizing the signals on the three-dimensional grid. Alternatively or in addition, the processing system receives MRI signals and the processing system and display device merges the color-coded three-dimensional image with respect to an anatomical image provided by the MRI, CT or other imaging signals.

In another aspect of the current disclosure, a frequency encoded source imaging system includes: a sensor array comprising a plurality of electrode and/or magnetic sensors where the sensor array is capable of being placed about a portion of a human body, and where the sensors are adapted to detect signals indicative of electrical/magnetic fluctuations present in the portion of the human body; and includes a processing system for analyzing the signals from the sensor array in a high-definition frequency band including frequencies greater than 70 Hz, where the analysis is localized with respect to a three-dimensional grid corresponding to the portion of the human body. Likewise it is an aspect of the current disclosure to provide a method for frequency encoded source imaging that includes the steps of (a) providing a sensor array that includes a plurality of electrodes and/or magnetic sensors; (b) detecting by the sensors signals indicative of electrical/magnetic fluctuations present in a portion of a human body about which the sensor array is arranged; (c) analyzing the signals from the sensor array in a high-definition frequency band including frequencies greater than 70 Hz; and (d) localizing the analysis with respect to a three-dimensional grid corresponding to the portion of the human body.

In a more detailed embodiment the processing system and a display device are configured to display a color-coded three-dimensional image corresponding to the localized analysis of the signals in the high-definition frequency band. In yet a further detailed embodiment, the three-dimensional grid includes a plurality of grid positions, and the processor is configured, for each grid position, to analyze and quantify the frequency signature and source strength for the high-definition frequency band.

Alternatively or in addition, the processing system includes at least two parallel processing pipelines, a first pipeline dedicated at least in part to the analyzing the signals from the sensor array in the high-definition frequency band, and a second pipeline dedicated at least in part to localizing the signals on the three-dimensional grid. Alternatively or in addition, the processing system receives MRI, CT or other signals and the processing system and display device merges the color-coded three-dimensional image with respect to an anatomical image provided by the MRI signals.

It is yet another aspect of the current disclosure to provide a multiple frequency encoded source imaging system that includes: at least two frequency range and two sources; at least two sensors, where each of the sensors detect primary signals emitted by a corresponding one of the at least two sources and cross scatter radiation from at least one of the other at least two sources and produces an aggregate signal including both of the detected primary signals and the detected cross scatter signals; and a computer pipeline which, based on the different contour map patterns, extracts from at least one of the aggregate signals the detected primary signal and associates the extracted primary signal with the corresponding signal source.

In a more detailed embodiment, the system further includes a reconstruction system that reconstructs the primary signal to generate an image of a functional activity within an imaging region. Alternatively or in addition, each of the different contour map patterns is driven at different frequency with respect to each other to uniquely frequency encode the signal source. Alternatively or in addition, the different contour map patterns are code-modulated to uniquely encode the source signals. Alternatively or in addition, the different contour map patterns are phase shifted with respect to each other to uniquely phase encode the source signals. Alternatively or in addition, at least one of the different contour map patterns appear on at least 3 sensors. Alternatively or in addition, the different contour map patterns are driven at different frequency with respect to each other to uniquely encode source signals. Alternatively or in addition, the different contour map patterns are associated with two or more of different frequencies, phases, latency, and amplitudes with respect to each other to uniquely encode the source signals. Alternatively or in addition, the source localization method determines an intensity contribution from each of the at least two sources to the aggregate signal. Alternatively or in addition, the system further includes a common oscillator and/or a pattern generator that generates the different contour map patterns. Alternatively or in addition, one or more of the at least two sources includes a control grid that facilitates generating its contour map pattern. Alternatively or in addition, the source scan employs at least one of a subtraction technique, a Fourier transformation, or a wavelet decomposition to decouple the at least one signal from the aggregate signal. Alternatively or in addition, at least one of the different contour map patterns includes a sequence of one of substantially square, sinusoidal, triangular, and sine pulses. Alternatively or in addition, the system is one of medical imaging, animal imaging, non-destructive imaging, and industrial imaging tomographic method.

It is yet another aspect of the current disclosure to provide a method for imaging brain activity associated with epilepsy that includes: providing at least an EEG and/or MEG sensor array including a plurality of sensors; detecting by the sensors signals indicative of electrical and/or magnetic fluctuations present in a patient's brain about which the sensor array is arranged; and analyzing the signals from the sensor array in at least two different frequency bands; where a first one of the at least two different frequency bands comprises frequencies from 1 Hz to 70 Hz; and where a second one of the at least two different frequency bands comprises frequencies less than 1 Hz or comprises frequencies greater than 70 Hz.

These and other aspects or objects of the current disclosure will become apparent from the following description, the appended claims and the attached drawings.

DETAILED DESCRIPTION

Embodiments of the current disclosure localize and visualize electrical and/or magnetic signals in at least two frequency ranges or bands.

Figure 2:
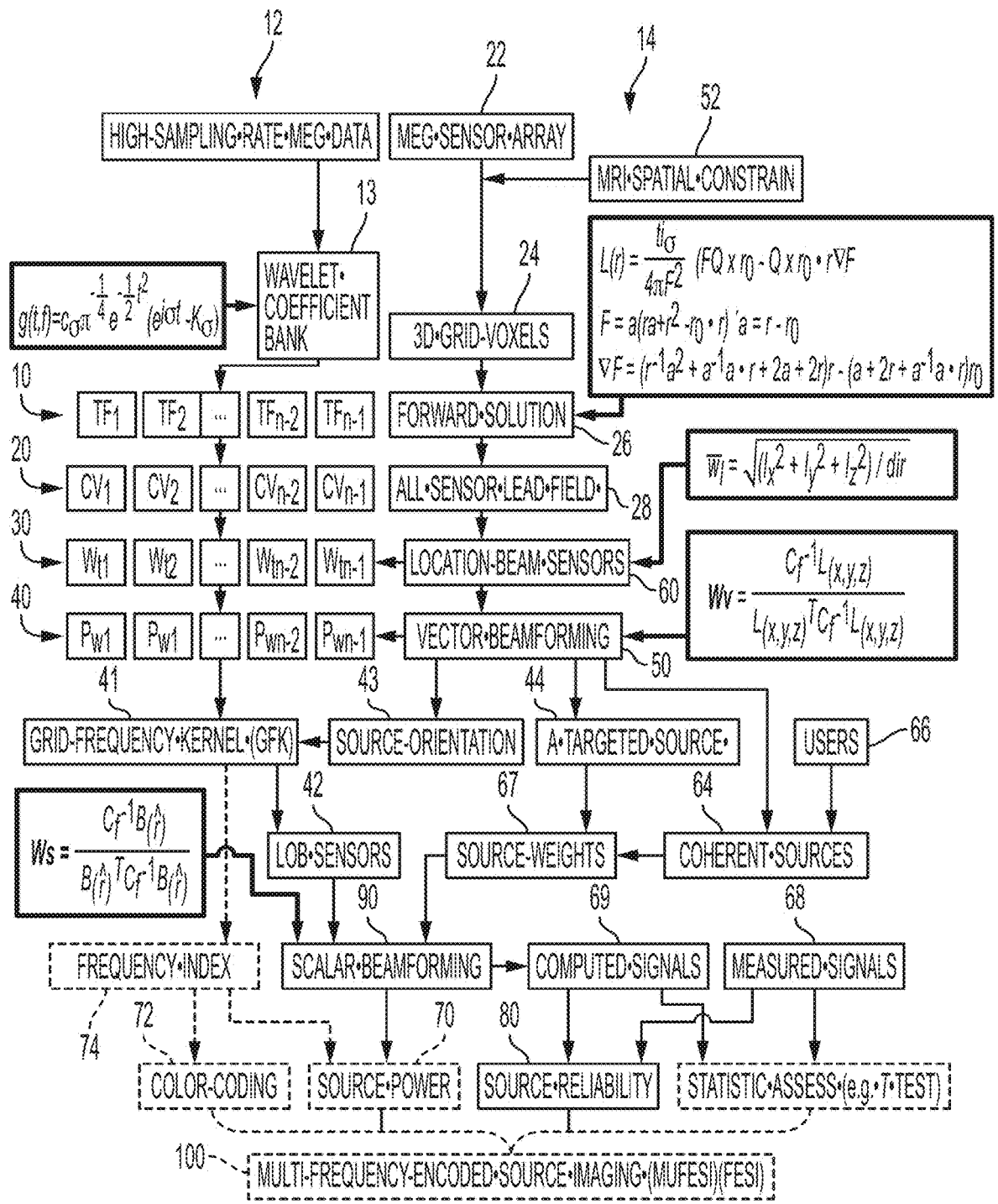
FIG. 2 is a block diagram representation of an exemplary multi-frequency encoded source imaging system according to an embodiment of the current disclosure.

FIG. 2 is a block-diagram representation of an exemplary system according to the current disclosure. The processing of multi-frequency signals (1, 2 . . . n-1) is shown on the left side 12. In blocks 10 "TF" indicates time-frequency; in blocks 20 "CV" indicates covariance; in blocks 30 "W" indicates weights estimated with lead fields; in blocks 40 "P" indicates source power estimated with vector-beamforming. "LOB" indicates location-orientation beam. Each frequency band (bin) has the same number of processing blocks/steps. The processing of source estimation is shown on the right side 14. Vector beamforming 50 in combination with location-beam sensors 60 estimates source orientation 43 and coherent sources 64. The source power 70 and source reliability 80 are based on the results of scalar beamforming 90. The processes 12/14 are parallel and characterized with multi-parameters per location (or voxel). The final step/block 100 is to generate a frequency encoded source imaging (FESI) for multi-frequency brain signals.

The signals are typically detected by a sensor array 22 (such as, but not necessarily limited to, an EEG or MEG sensor array), which include at least two electrodes and/or magnetic sensors. Several frequency sources in a magnetoencephalography system or electroencephalography system are placed over the portion of the body such as the brain or the chest (or other area of interest) of the subject being imaged. The data acquisition system should have fiducial points for accurate localization of the source and for overlapping with structural images such as magnetic resonance imaging (MRI) 52. Embodiments of the current disclosure will analyze signals in multiple (>2) frequency bands from very low to very high (e.g., from 0.0000001 Hz to 3,000 Hz), and perform volumetric scan the sources of the signals in each frequency band. To scan sources for signals in multiple frequency bands, a three-dimensional (3D) grid 24 will be created for a source image. Sources at each position of the 3D grid will be analyzed. The frequency signature, source strength will be analyzed, quantified and stored for each position. Embodiments of the current disclosure further include the function to have multiple-parameters per position within the 3D grid. Each position within the 3D grid will become as a voxel in the resulted source image. If signals from more than one frequency bands are from the same grid position, signals with higher frequency will take the priority by default although the user of this method can change this behavior.

To improve the performance of time-frequency transform, Wavelet-Coefficient Bank 13 is a set of wavelet-coefficients that can be computed before data analyses. By using Wavelet-Coefficient Bank, the same wavelet-coefficient can be used for analyzing multiple datasets without computing wavelet coefficients for every dataset.

Grid-Frequency Kernel (GFK) 41 is a data matrix, which is used to store some key information (e.g. the position and frequency indices) at the center of data processing pipelines (e.g., for computing the source strength and probability of brain activity).

LOB Sensors (42) are a set of sensors that are picked by using the lead field optimized beamforming techniques.

Since MEG and EEG are typically used to analyze signals from the human body, signals from other places (e.g., magnetic signals from environmental noise) are typically ignored or not important. To exclude those noises or signals which are not important, MRI-Spatial-Constrain 52 can be used to limit the data processing to signals from certain spatial regions (e.g., the regions of cerebral cortex revealed by MRI).

Source-Orientation 43 is the orientation of sources estimated by vector beamforming. The source that is currently analyzed for source strength and probability is A Targeted Source 44.

The data analysis pipeline provide a way for user to manually add or remove some data processing workflows. For example, Users 66 can add coherence function to analyze the coherent-sources 64.

The Source-weights 67 enables the source analysis is performed for brain areas that are more important for clinicians or users (e.g. the motor cerebral cortex may be critical for brain surgery and sources from the motor cortex need to be carefully analyzed).

The Computed Signals 69 are the signals computed with scalar beamforming for sensors that are linearly related to the source activity. The Measured Signals 68 are the signals that are truly measured or detected by physical sensors.

To distinguish sources in different frequency bands, each frequency of the sources may be encoded with a unique color (or pattern, or texture) in box 72 based on a frequency index 74. Embodiments of the current disclosure further include at least two sets of color (or pattern or texture) tables 74 for encoding frequency and other parameters for visualization of source signals in multiple frequency bands. Multiple color-coding may provide the capability to visualize the strength and frequency signatures of the source signals at each position of the 3D grid. Embodiments of the current disclosure may provide 3D patterns for clinicians to identify lesions or dysfunctions in the human body including in brain, heart and other organs. Since signals in medical fields are typically in a narrow and median (e.g. brain signals in 3-70 Hz) frequency range, signals in the low and high frequency ranges may be new biomarkers for clinical diagnosis and treatment.

With a conventional single frequency source scan, the signals recorded from a sensor array are limited to one frequency range or band. In particular, the signals from the brain or heart are conventionally digitalized in a narrow frequency range and are then analyzed in one frequency range, which is commonly in 1-70 Hz. Embodiments of the current method, software and hardware, provide a capability to digitize signals in a very wide frequency range, which can be 0.0000001 Hz to 20,000 Hz. The signals digitized in the wide frequency range will then be divided into multiple frequency range, for example, 0.1-1 Hz, 1-4 Hz, 4-8 Hz, 8-12 Hz, 13-30 Hz, 14-70 Hz, 30-60 Hz, 60-90 Hz, 90-250 Hz, 250-600 Hz, 600-1,000 Hz and 1,000-3,000 Hz.

Signals recorded for multiple frequency analyses (or multi-frequency analysis, MFA) require high sampling rates, which requires to be at least 2-4 time higher than the analysis frequency. For example, to analyze signals in 1,000-3,000 Hz, the sampling rate will be 12,000 Hz. The size of high simple rate data is typically very big. For example, two minutes recordings of 275 channel magnetoencephalography data will be around 2 GB data, several hour recording of high sample MEG data will reach 1 to 2 TB data.

In view of the foregoing, software and hardware (or a system) may be needed to acquire, analyze and store the huge amount of high sampling data for multiple frequency analysis.

Aspects of the current disclosure address these matters, and others.

According to one aspect, a set of algorithms are illustrated. The high sampling rate apparatus includes at least the capability to turn off all online-filtering, which enables researcher, clinicians or any other users to perform offline filters. A minimum sampling rate of 500 Hz may be necessary for certain embodiments. Since signals from the human body, such as the brain, can occur in different frequency ranges and different frequencies may have different corresponding amplitudes, we used a different sigma value for each frequency to capture the time-frequency changes. Consequently, wavelet equation can be represented as follows:

$$G(t,f) = C_\sigma \pi^{-1/4} e^{-1/2 t^2} (e^{i\omega t} - \kappa_\sigma) \quad (1)$$

In the formula, t indicates time and $f$ indicates frequency. Each wavelet transform has its own sigma value. Sigma is the scaling parameter that affects the width of the window. The sigma values are derived from the mother function in wavelet transform by computing the number of small waves for a time-frequency analyses. Sigma values could also be experimentally determined. $\kappa_\sigma$ represents the admissibility and $C_\sigma$ represents a normalized constant. $\sigma$ represents the standard deviation of the Gaussian curve in the time domain. If signals appeared in the given sensitive time (a small sigma value) and sensitive frequency (a large sigma value) ranges, they would be enhanced.

An accumulated spectrum was defined as the time-frequency summation of a long-time or continuous recording which has a time period at least two times longer than that of the time window of the spectrum. The equation of computing accumulated spectra is given by:

$$Atf(s, f) = \sum_{t=1}^{T} \sum_{f=1}^{F} G(t, f) \quad (2)$$

In equation 2, $Atf$ represents an accumulated spectrum; s indicates the time slice of the spectrum; $f$ indicates frequency bands (or bins) of EEG/MEG data; T indicates total time points of EEG/MEG data and F indicate the total frequency bands. We defined $s \geq 1$ and $s \leq T/2$. From computer program point of view, the use of computer memory and storage space by equation 2 depends on the s. Even though T could be infinitively increasing, the requirements for computer memory and storage remain the same. Consequently, the approach automatically avoided possible "overflow" or "out of space" problems in a long-time or continuous recording for capturing epileptic activity.

An accumulated spectrogram can be computed by sequentially transforming each of the segments of waveform data to time-frequency representations using Morlet wavelet algorithm and then accumulating all the spectra together. In this procedure, the different spectrograms of individual time segments were mathematically summed together to a single new overall spectrogram. An accumulated spectrogram can reveal brain activity in a consistent frequency range at multiple time windows. It can be considered as a "collective result" for a long-time recording.

One potential usage of this technology is to analyze signals in magnetoencephalography. The neuromagnetic activity at each sensor can be visualized with contour maps, which showed small spectrograms at the position of each MEG sensor in the array 22. The equation of computing global spectrogram is given by:

$$G(s, f) = \frac{1}{M} \sum_{m=1}^{M} Aft(s, f) \quad (3)$$

In equation 3, G represents the global spectrogram; $Atf$ represents an accumulated spectrum of one magnetic sensor data; m indicates magnetic sensor index and M indicates the total number of magnetic sensors; s indicates the time slice of the spectrum; $f$ indicates frequency bands (or bins) of magnetic data.

To localize multiple frequency signals at source levels, two computing pipelines are included in the new technology. One computing pipeline 12 generates multi-frequency datasets by processing data with filter or wavelet transforms. Signals in multi-frequency datasets are in a set of frequency ranges. Of note, the frequency ranges depends on the research tasks and can be predefined. Another computing pipeline 14 performs four tasks: (1) creating a three-dimensional source grid (3D grid) 24, where each grid node represents a possible source; (2) conducting forward solution 26 by calculating lead fields for each source (node) for the entire grid; (3) computing the lead field norm (or magnitude) and ranking the norm for each source for all sensors; (4) producing the node-beam lead field 28, performing single value decomposition and calculating spatial filter weights. The node-beam lead field 28, which represents a form of sub-space solution, is completed by selecting a group of sensors which had a larger lead field norm.

Differing from the conventional volumetric source imaging or distributed source map, each grid node consists of multiple data items including the strength and frequency of the source activity. The mathematic relationship between measured MEG data and source activity can be expressed as following equation:

$$B = LQ + N \quad (4)$$

In Equation 4, B represents the MEG data; L represents the lead field, Q represents the source strength, and N represents the noise. For a given MEG dataset, B is known and L can be computed for each node with a forward solution. Under these assumptions, we propose using Single Value Decomposition (SVD) to decompose the lead field as following:

$$L = USV^T \quad (5)$$

Where $U \in R^{m \times m}$ is an orthogonal (unitary in the complex case) matrix. The columns of U are the left singular vectors of L. $V \in R^{m \times m}$ is an orthogonal (unitary in the complex case) matrix. The columns of V are right singular vectors of L. $S = \text{diag}(\sigma_1, \sigma_2, \ldots \sigma_p)$ is an M×N diagonal matrix with $p = \min(m,n)$ and $\sigma_1, \sigma_2, \ldots \sigma_p$ are the singular values of L. M indicates the number of sensors and N indicates the number of source orientations. For a single source, p is $\leq 3$. The Moore-Penrose pseudo inverse of L is given by:

$$L^+ = VS^+ U^T \quad (6)$$

Where $S^+$ is a diagonal formed with the multiplicative inverses of the non-zero singular values of L placed on the diagonal. Assuming there was no noise (N=0), the measured MEG data, B, can be described by the following equations:

$$B = LQ = USV^T Q \quad (7)$$

$$Q = BL^{-1} \quad (8)$$

By replacing $L^{-1}$ in equation 8 with L in equation 8, the estimated moment, $\vec{Q}$, can be computed with a SVD back substitution as described in the following equation:

$$\vec{Q} = BVS^+ U^T \quad (9)$$

Of note, $L^+$, pseudo inverse of L, could be computed once and used for the analysis of data in all frequency ranges, which makes the computation of source strength and probability more efficient. In addition, once the $\vec{Q}$ is determined, virtual sensor spectrograms can be also computed with $\vec{Q}$ for each frequency range and time window.

$$V(t, f) = \sum_{t=1}^{T} \sum_{f=1}^{F} \|\vec{Q}\|_2 (TF)^{-1} \quad (10)$$

In equation 10, V represents the computed virtual sensor spectral data. The t and T indicate time slice and total number of time windows, respectively. The $f$ and F indicate frequency band and total number of frequency bands, respectively. Magnetic signals generated by $\vec{Q}$ can be computed with the follow equation:

$$X_{cmp} = L\vec{Q} \quad (11)$$

where Xcmp represents computed magnetic signals at individual sensors from source $\vec{Q}$. We used Xmea to represent the measured magnetic signals at individual sensors, which were different from B in equation 3, which represents data in general.

Figure 1:
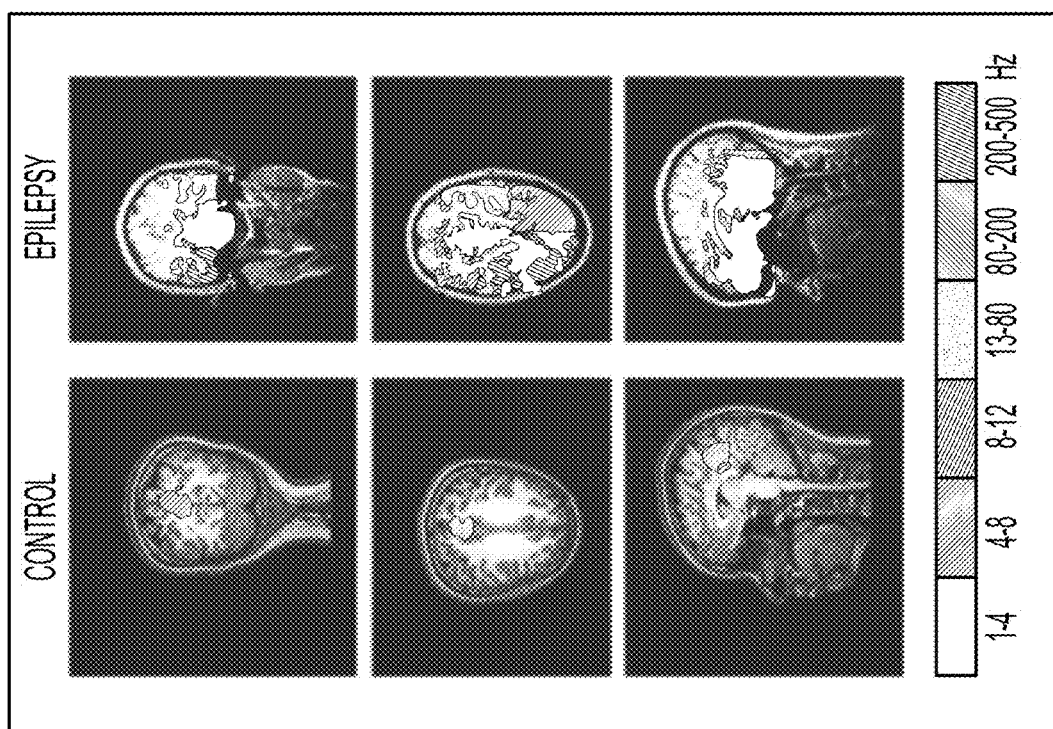
FIG. 1 illustrates exemplary images showing multi-frequency encoded source imaging according to an embodiment of the current disclosure.
Figure 1:
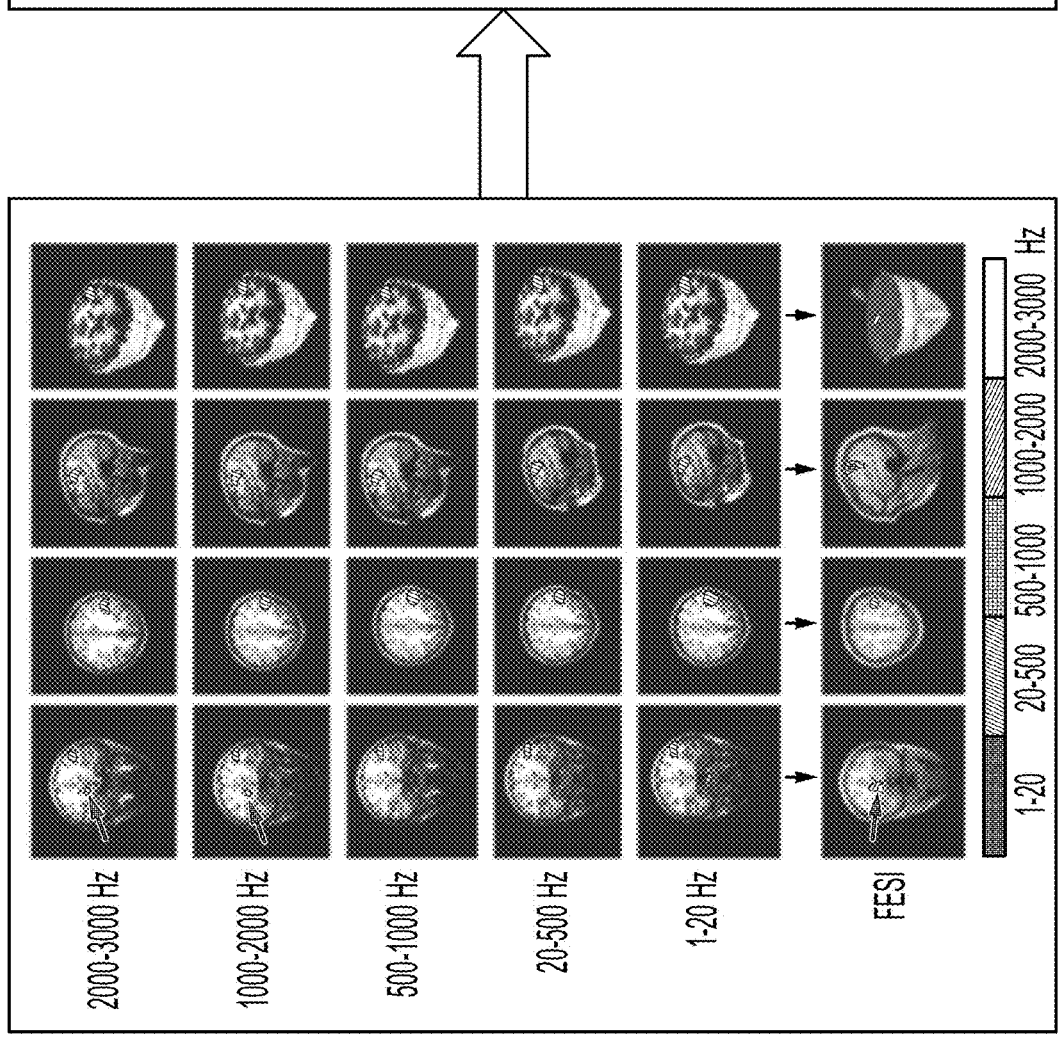

FIG. 1 illustrates an exemplary images showing multi-frequency Encoded Source Imaging (MUFESI) according to embodiments of the current disclosure. This case shows epileptic activities in multiple frequency ranges (bands), which helps neurosurgeons to remove the epileptogenic zones. The patient is seizure free after surgery.

Figure 3:
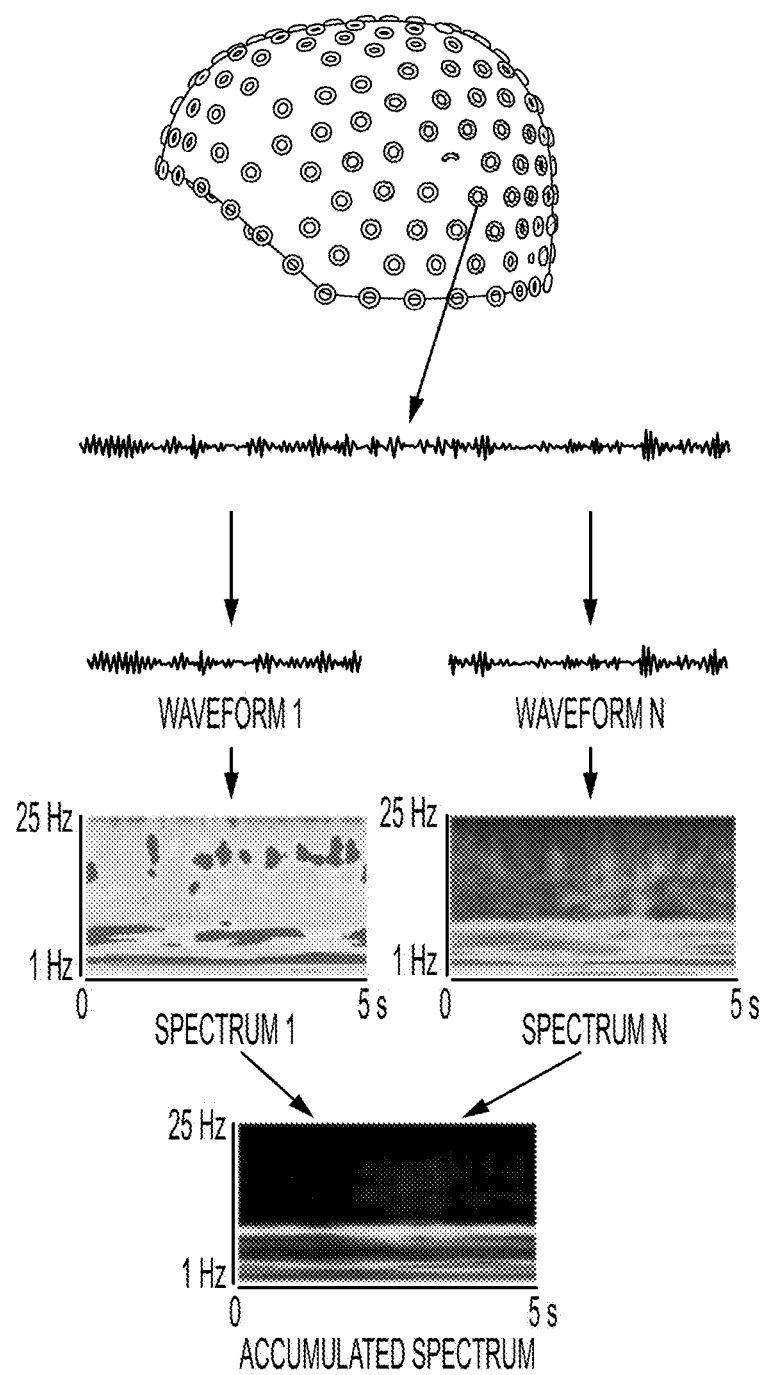
FIG. 3 illustrates processing steps according to an exemplary process of the current disclosure.

FIG. 3 illustrates exemplary a new approach for efficiently processing signals in a broad band frequency range. Multiple frequency signals are recorded with a sensor array. Each sensor generate a multiple frequency signal. The new technology can analyze the time-frequency representation of signals (spectra) in a long recording (e.g., 120 seconds or 20-30 minutes) by dividing the entire recording into multiple segments (e.g., Waveform 1, Waveform 2, . . . Waveform N, each segment has 1 second or longer). After completing time-frequency analyses for all segments, the approach will add all spectra together to form an accumulated spectrogram.

Figure 4:
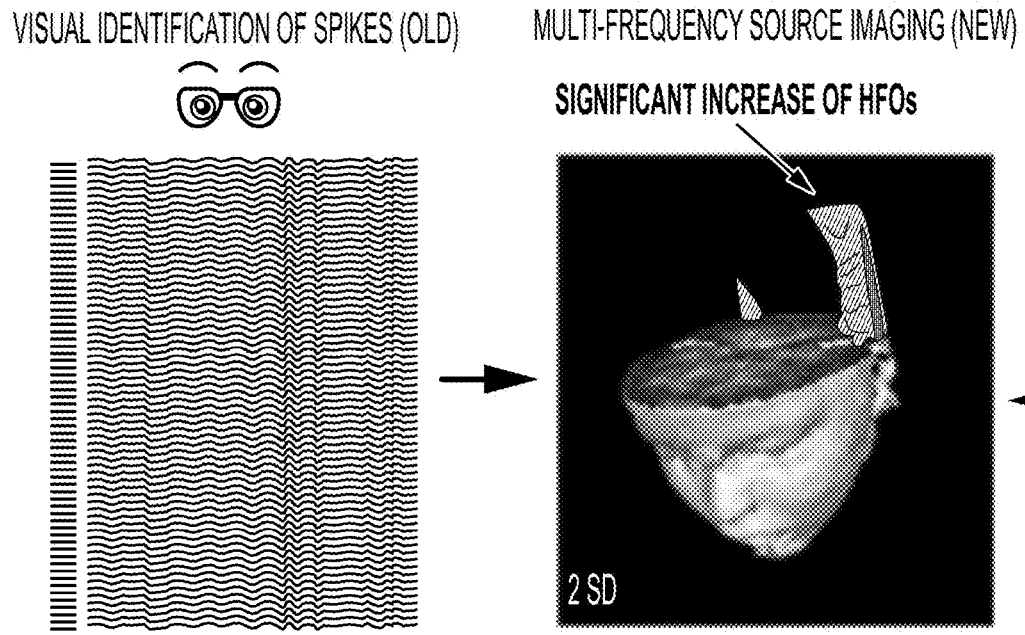
FIG. 4 illustrates an exemplary output image according to an exemplary embodiment versus the conventional art.

FIG. 4 illustrates an exemplary 3D visual display output 200 for an embodiment of the current disclosure in comparison with conventional output. Conventionally, epileptic abnormality is visually identified, which is subjective. The new method can generate a volumetric imaging to quantify the epileptic abnormality, which is objective. From methodological point of view, this method can make changes to the clinical routine, from visual identification of spikes to automated quantitative images of brain aberrations.

Figure 5:
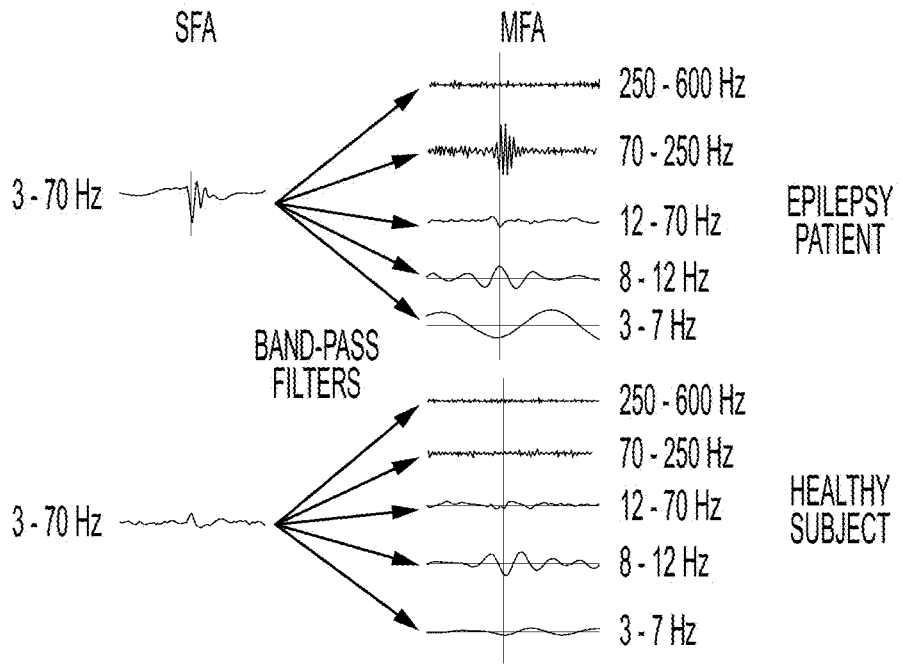
FIG. 5 illustrates processing steps according to an exemplary process of the current disclosure.

FIG. 5 illustrates a first exemplary waveforms of multiple frequency signals. The multiple frequency components can be visualized by multiple filters.

Figure 6:
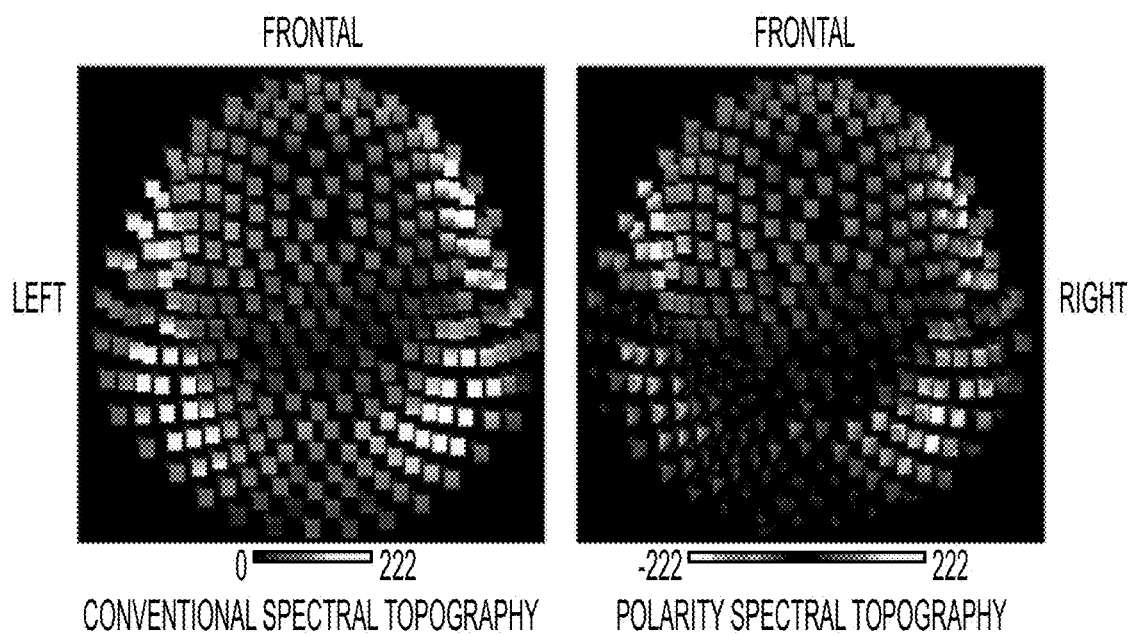
FIG. 6 illustrates another exemplary output image according to an exemplary embodiment versus a conventional output image.

FIG. 6 illustrates exemplary contour map patterns for uniquely spectral encoding the signals originated from the brain to demonstrate the embodiments of the current disclosure in clinical applications as compared to conventional mapping.

Figure 7:
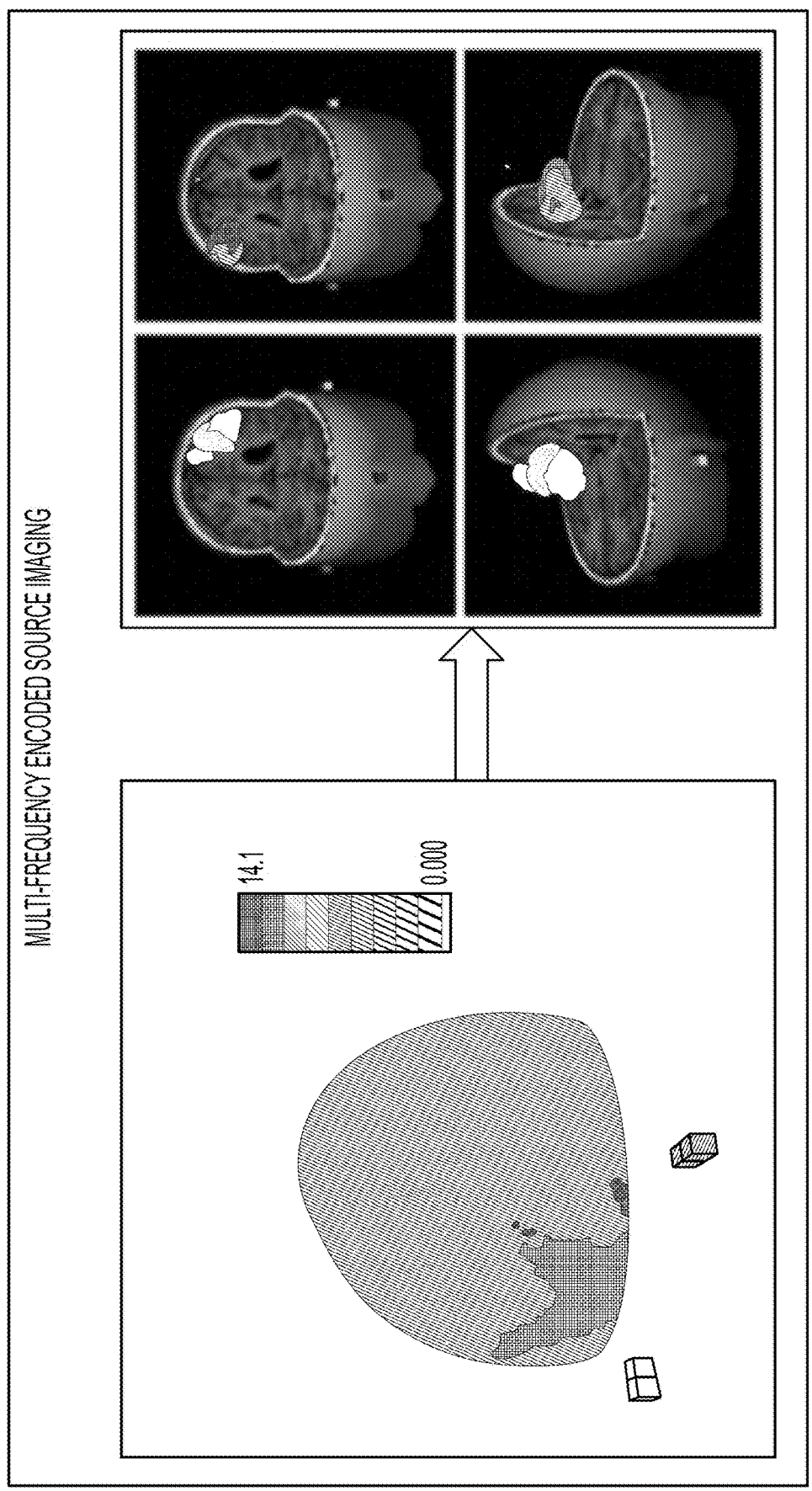
FIG. 7 illustrates another exemplary output image and illustrates associated processing steps according to an exemplary embodiment.

FIG. 7 illustrates an exemplary results for multi-frequency encoded source imaging according to the current disclosure. The new technology can localize and visualize the somatosensory in the brain for pre-surgical functional mapping.

Figure 8:
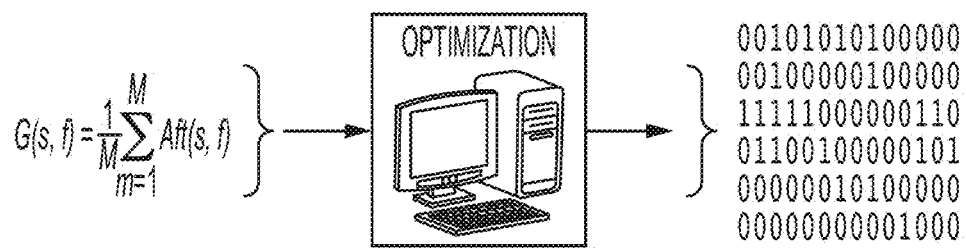
FIG. 8 illustrates an exemplary process for optimizing performance of various embodiments.

FIG. 8. Illustrates an exemplary method for improving the performance of the method. In addition to aforementioned algorithms, aspects of the current disclosure can be implemented in software, which can be optimized with new computer technologies to make the data analysis faster and more efficient.

Figure 9:
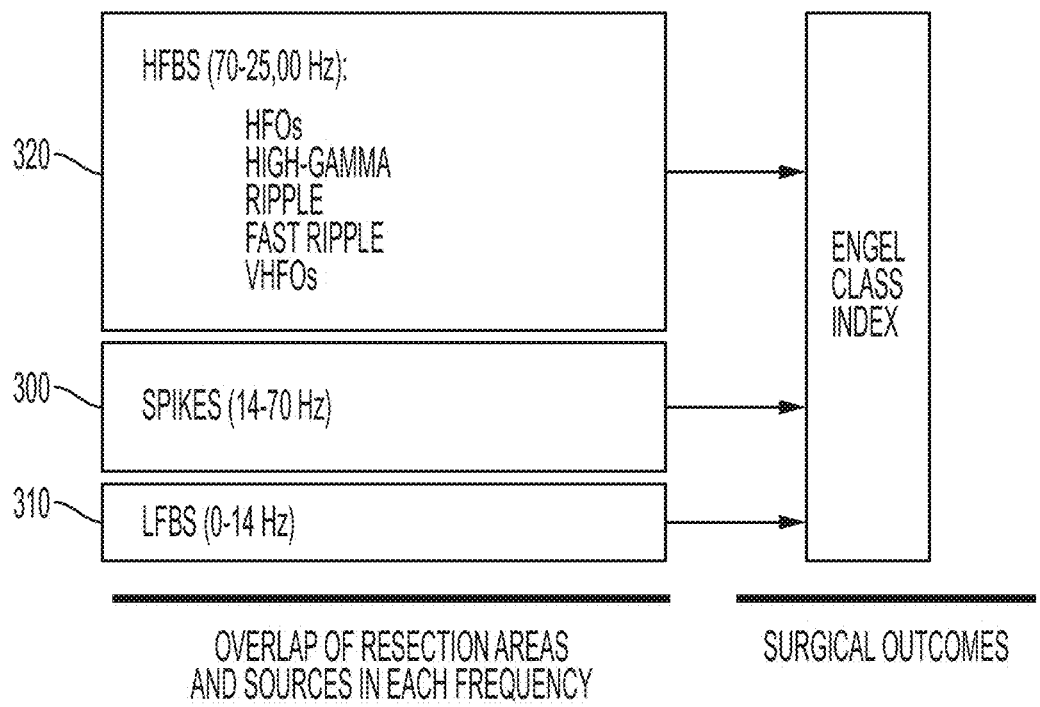
FIG. 9 illustrates a multi-frequency analysis approach for epilepsy according to an exemplary embodiment.

FIG. 9. Illustrates an exemplary applications of the new technology in changing the outcomes of epilepsy surgery. The conventional approach can only use the spikes 300 for epilepsy surgery, exemplary approaches disclosed herein can use brain signals from very low 310 to very high frequency range 320 for epilepsy surgery.

Embodiments of the current disclosure employ multiple data analysis threads to localize signals from body in multiple frequency ranges. The multiple frequency signals emitted by each source is uniquely encoded (e.g., via frequency, phase, amplitude, and/or latency encoding). A broad frequency detector detects primary signals emitted by a corresponding source and cross scatter signals emitted by other sources and generates an aggregate signal, which includes signal components indicative of the detected primary and cross scatter signals. The unique encoding of the signals can be used to decouple or otherwise extract one or more of the individual signal components from the aggregate signal.

The new method includes several steps to localize sources.

In one implementation, frequency encoding is used so that the various sources are analyzed and localized in multiple frequencies. In addition to frequency encoding, other encoding techniques such as code, phase, amplitude, and latency cycle encoding (either alone or in various combinations) are contemplated. Such encoding is performed so that two or more of electrical and magnetic sources can be concurrently operated to simultaneously.

In another embodiment, several frequency sources in a magnetoencephalography system or electroencephalography system are placed over the portion of the body such as the brain or the chest of the subject being imaged. The data acquisition system should have fiducial points for accurate localization of the source and for overlapping with structural images such as magnetic resonance imaging (MRI).

Figure 10:
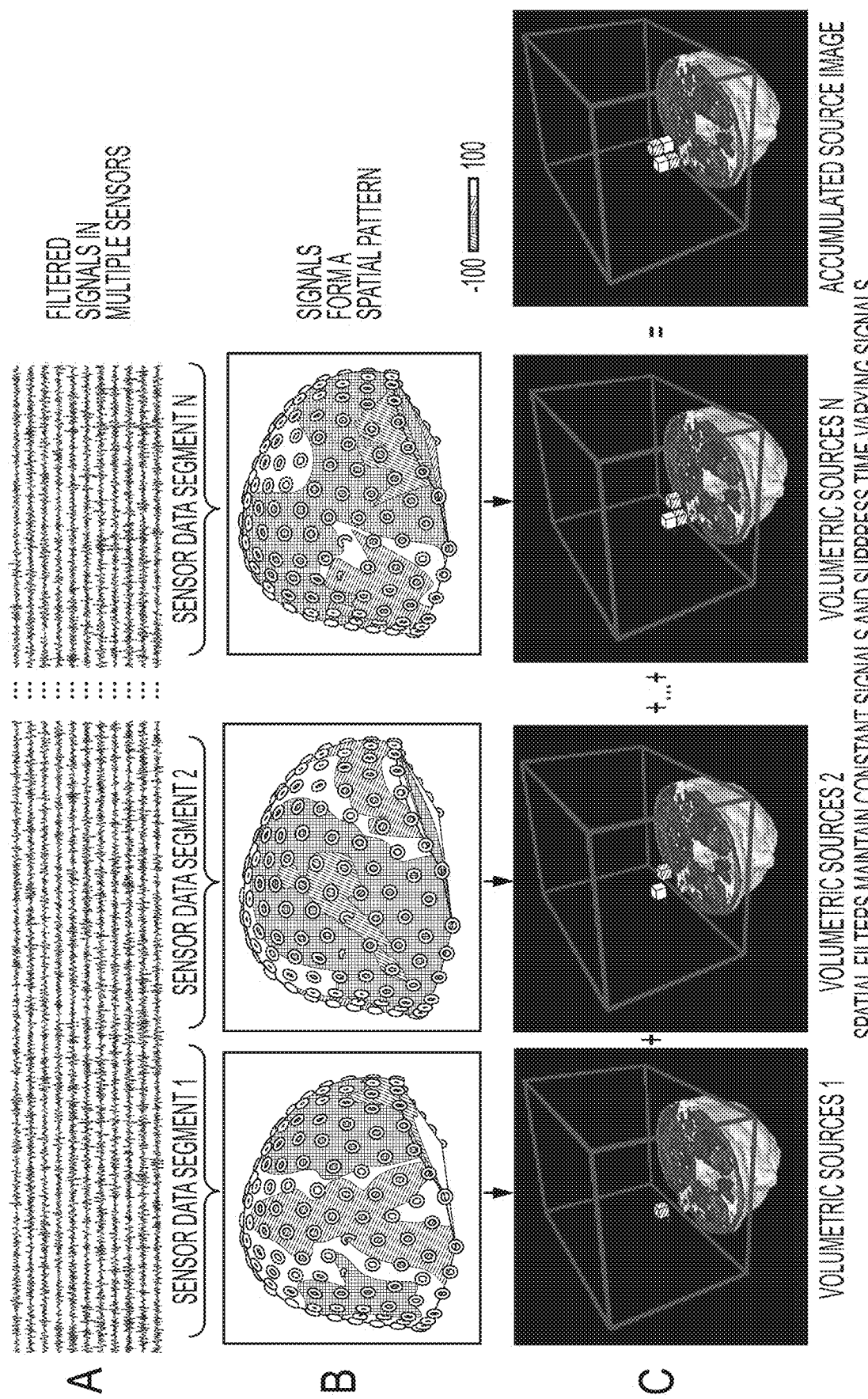
FIG. 10 illustrates an exemplary method for accumulating consistent sources and further illustrates another exemplary output according to an exemplary embodiment.

FIG. 10. Illustrates an exemplary method for accumulating consistent sources. The signals from the various sensors are provided to be recorded in several channels ("A"). In one implementation suitable for use with frequency encoded signals, lock-in amplifiers are used to "lock-in" on one or more of the signals and according reference pattern/modulation frequency within the aggregate signal. When using the lock-in amplifiers, both the aggregate signal and the switching pattern, via a SYNC connection, that corresponds to a signal of interest are provided to the lock-in amplifier. The lock-in amplifier multiplies the aggregate signal by one of the switching patterns that are visualized as contour maps or spatial patterns ("B").

The product of the aggregate signal is processed by multiple band-pass filters. The spatial filters pass constant signals ("C") and suppresses time-varying signals. The constant signals are from true sources within the brain while the time-varying signals are typically noise which are typically from areas that are out of the brain.

As previously discussed, a different contour map pattern (or spatial pattern) can be used for each of the signal sources in order to uniquely encode each of the sources. An exemplary frequency encoding scheme will be described in relation to a system having multiple sources. The frequency may depend on the operation mode, a maximum data acquisition speed, and/or the sensor array. A typical frequency would be in the hundred Hz to few kHz range adapted to the maximum readout frequency of the detector system to avoid under sampling.

An alternative to the frequency encoding described above is phase encoding. FIG. 6 illustrates exemplary phase encoded patterns.

Using the techniques described herein, the extracted signal(s) is associated with its one of the sources.

The systems and/or methods described herein and/or derivations thereof can be applied in medical imaging applications such as, but not limited to, magnetoencephalography, electroencephalography, and electrocardiography.

The invention has been described with reference to the exemplary embodiments. Of course, modifications and alterations will occur to others upon reading and understanding the preceding description. It is intended that the invention be construed as including all such modifications and alterations insofar as they come within the scope of the appended claims.

What is claimed is:

1. A frequency encoded source imaging system, comprising:
    an array of electrodes and magnetic sensors, the array being (i) distributed over a portion of a body and (ii) configured to detect signals indicative of at least one of electrical and magnetic fluctuations at the bodily portion; and
    a processing system configured to analyze the detected signals in at least (i) a first frequency range less than a first threshold and (ii) a second frequency range greater than a second threshold, the first threshold being less than the second threshold, wherein the analysis is localized with respect to a three-dimensional (3D) grid corresponding to the bodily portion.

2. The system of claim 1, wherein the first threshold is 14 Hz and the second threshold is 70 Hz.

3. The system of claim 1, further comprising a display device coupled to the processing system,
    wherein the processing system and display device are configured to display a color-coded 3D image corresponding to the localized analysis of the signals in the frequency ranges,
    wherein the 3D grid includes grid positions, a processor being configured, for each grid position, to analyze and quantify a frequency signature and source strength for each of the frequency ranges, and
    wherein the display device displays a color corresponding to the respective frequency range having a criterion-satisfying parameter for each grid position.

4. The system of claim 1, wherein the processing system includes at least two parallel processing pipelines, and
    wherein a first pipeline is dedicated at least in part to the analysis and a second pipeline is dedicated at least in part to the localization.

5. The system of claim 1, wherein the system is at least one of an electroencephalography system and a magneto-encephalography system.

6. The system of claim 3, wherein the processing system receives magnetic resonance imaging (MM) signals, and
    wherein at least one of the processing system and the display device merges the color-coded 3D image with respect to an anatomical image provided by the MRI signals.

7. The system of claim 1, further comprising a reconstruction system that reconstructs a primary signal to generate an image of a functional activity within an imaging region.

8. The system of claim 3, wherein the parameter relates to signal source strength.

9. The system of claim 3, wherein the parameter relates to probability of brain activity.

10. The system of claim 1, wherein each node of the 3D grid represents a possible signal source.

11. The system of claim 1, further comprising a computer which obtains different contour map patterns by encoding each primary signal with a unique pattern, the unique pattern being associated with a respective position along a contour of body portions.

12. The system of claim 11, wherein the different contour map patterns are code-modulated to perform the encoding.

13. The system of claim 11, wherein the different contour map patterns are phase shifted with respect to each other to perform the encoding.

14. The system of claim 11, wherein at least one of the different contour map patterns appears on at least three of the array.

15. The system of claim 11, wherein the different contour map patterns are associated with two or more of different frequencies, phases, latency latencies, and amplitudes with respect to each other to perform the encoding.

16. The system of claim 1, further comprising at least one of a common oscillator and a pattern generator that generates different contour map patterns.

17. The system of claim 1, wherein a source scan employs at least one of a subtraction technique, a Fourier transformation, and a wavelet decomposition to decouple at least one signal from an aggregate signal.

18. The system of claim 1, wherein at least one of the different contour map patterns includes a sequence of one of substantially square, sinusoidal, triangular, and sine pulses.

* * * * *